(12) United States Patent
Crowley

(10) Patent No.: US 10,525,093 B2
(45) Date of Patent: Jan. 7, 2020

(54) CANNABINOID FORMULATIONS AND METHOD OF MAKING THE SAME

(71) Applicant: Farm to Farma, Inc., Incline Village, NV (US)

(72) Inventor: Kenton L. Crowley, Temecula, CA (US)

(73) Assignee: FARM TO FARMA, INC., Incline Village, NV (US)

( * ) Notice: Subject to any disclaimer, the term of this patent is extended or adjusted under 35 U.S.C. 154(b) by 0 days.

(21) Appl. No.: 15/812,770

(22) Filed: Nov. 14, 2017

(65) Prior Publication Data

US 2018/0133272 A1     May 17, 2018

Related U.S. Application Data

(60) Provisional application No. 62/421,933, filed on Nov. 14, 2016.

(51) Int. Cl.

| | |
|---|---|
| *A61K 36/00* | (2006.01) |
| *A61K 36/185* | (2006.01) |
| *A61K 31/05* | (2006.01) |
| *A61K 31/352* | (2006.01) |
| *A61K 31/4045* | (2006.01) |

(52) U.S. Cl.
CPC ............ *A61K 36/185* (2013.01); *A61K 31/05* (2013.01); *A61K 31/352* (2013.01); *A61K 31/4045* (2013.01)

(58) Field of Classification Search
None
See application file for complete search history.

(56) References Cited

U.S. PATENT DOCUMENTS

| | | |
|---|---|---|
| 2002/0048551 A1 | 4/2002 | Keller et al. |
| 2003/0013639 A1* | 1/2003 | Yurchak .................. A61K 31/28 424/690 |
| 2009/0162529 A1* | 6/2009 | Shi .......................... A23L 27/36 426/658 |
| 2012/0107300 A1 | 5/2012 | Schirripa |
| 2015/0105455 A1 | 4/2015 | Bjorncrantz |
| 2016/0166543 A1 | 6/2016 | Joshi et al. |
| 2017/0189463 A1 | 7/2017 | Franklin et al. |

FOREIGN PATENT DOCUMENTS

WO     2015160842 A1     10/2015

OTHER PUBLICATIONS

Alagbonsi et al, Melatonin and vitamin C exacerbate Cannabis sativa-induced testicular damage when administered separately but ameliorate it when combined in rats. Journal of basic and clinical physiology and pharmacology, (May 1, 2016) vol. 27, No. 3, (Year: 2016).*
Qureshi et al, Estimation of biologically active cannabinoids in Cannabis indica by gas chromatography-mass spectrometry (GC-MS). World Applied Sciences Journal (2012), vol. 19, No. 7, pp. 918-923 (Year: 2012).*
"Melatonin for Sleep: Does It Work?", John Hopkins Medicine, https://web.archive.org/web/20161002111712/https://www.hopkinsmedicine.org/health/healthy-sleep/sleep-science/melatonin-for-sleep-does-it-work, Oct. 2, 2016, pp. 1-5.
Moreno-Sanz , "Can You Pass the Acid Test? Critical Review and Novel Therapeutic 10 Perspectives of [Delta]9-Tetrahydrocannabinolic Acid A", Cannabis Cannbinoid Res., vol. 1, Issue No. 1 https://www.ncbi.nlm.nih.gov/pmc/articles/PMC5549534/, Jun. 1, 2016, pp. 124-130.
PCT/US2017/061584 , "International Search Report and Written Opinion", dated Feb. 2, 2018, 12 pages.

* cited by examiner

*Primary Examiner* — Qiuwen Mi
(74) *Attorney, Agent, or Firm* — Kilpatrick Townsend & Stockton LLP

(57) ABSTRACT

A composition comprising cannabis extract and melatonin is provided, along with formulations for delivering the composition to a subject. The composition can include a base ingredient such as polyethylene glycol, gelatin, tapioca and/or pectin; natural sweeteners; and oils of peppermint, lavender, ginger, citrus, mango, etc. The formulation can include tablets, capsules, lozenges, troches, suppositories, tinctures, a transdermal patch, a vaporizer, a metered dose inhaler, etc. The formulation avoids harmful preservatives (e.g., BHT, BHA), heavy metals and stabilizers while addressing sub-therapeutic dosing and optimizing the synergistic qualities of the ratios of the individual cannabinoids (both acidic and neutral forms), terpenes and flavonoids.

20 Claims, No Drawings

CANNABINOID FORMULATIONS AND METHOD OF MAKING THE SAME

CROSS-REFERENCES TO RELATED APPLICATIONS

This application claims the benefit of priority to U.S. Provisional Patent Application No. 62/421,933, filed Nov. 14, 2016, which is incorporated by reference herein.

FIELD OF THE INVENTION

The present disclosure relates to compositions comprising cannabinoids and melatonin, and formulations and products suitable for administering effective doses of the compositions to a subject.

BACKGROUND OF THE INVENTION

Cannabis, commonly known as marijuana, hemp, and by numerous other names, is a preparation of the cannabis plant intended for use as a psychoactive drug and as medicine. Pharmacologically, the principal psychoactive constituent of cannabis is tetrahydrocannabinol (THC) representing one of hundreds of known compounds in the plant, including many other cannabinoids, such as cannabidiol (CBD), cannabinol (CBN), tetrahydrocannabivarin (THCV) and cannabigerol (CBG). The use of both neutral and acid forms of the cannabinoids results in distinctly different therapeutic endpoints.

While certain of the cannabinoids are known to help with certain medical conditions, the illegality of cannabis has prevented wide spread usage for medical conditions. On the other hand, recreational, illegal use has flourished. However, as more and more states legalize cannabis for medical use, there is a need to develop cannabis for the efficient and effective treatment of many medical conditions.

Many cannabis-based products contain harmful preservatives (e.g., BHT, BHA), and stabilizers, artificial flavorings, colors, mycotoxins, simple sugars, as well as toxic byproducts (e.g., Benzene, Hexane, heavy metals, etc.) from extraction methods, and/or trigger side effects and fail to provide effective relief for the subject medical condition.

BRIEF SUMMARY OF THE INVENTION

Provided herein are compositions and formulations comprising cannabis extract and melatonin. In some embodiments, the composition or formulation is a pharmaceutical composition or pharmaceutical formulation. In some embodiments, the melatonin is present at a concentration of 0.05% to 1.6% by weight of the composition and/or formulation. In some embodiments, the compositions described herein are provided in a suitable delivery system or formulation for administering to a subject, such as but not limited to a tablet, capsule, lozenge, troche, tincture, transdermal patch, vaporizer, or metered dose inhaler. In some embodiments, the melatonin is present at 0.5 mg to 16 mg per individual formulation or dose (for example, from 0.5 mg to 16 mg per individual tablet, capsule, lozenge, troche, tincture dose, transdermal patch, or per inhalation from a vaporizer or metered dose inhaler). In some embodiments, the compositions described herein are provided as a suitable product for consumption by a subject, such as but not limited to a tablet, capsule, lozenge, troche, tincture, transdermal patch, vaporizer, or metered dose inhaler. In some embodiments, the dose of melatonin is 0.5 mg to 16 mg in each individual product that is capable of being consumed by or administered to a subject.

In some embodiments, the cannabis extract comprises tetrahydrocannabinol (THC), and/or other cannabinoids, such as cannabidiol (CBD), cannabinol (CBN), tetrahydrocannabivarin (THCV) and cannabigerol (CBG) (at least 144 cannabinoids have been identified at the time of this application). In some embodiments, the extract comprises natural, neutral, or acidic forms of the cannabinoids, or semi-synthetic and synthetic derivatives thereof. In some embodiments, the cannabis extract comprises terpenes and/or flavonoids.

In some embodiments, the composition or formulation further comprises a base selected from polyethylene glycol (PEG), gelatin, agar, tapioca, pectin, fatty acid and wax. In some embodiments, the composition or formulation comprises PEG. In some embodiments, the composition or formulation comprises gelatin. In some embodiments, the composition or formulation comprises pectin. In some embodiments, the composition or formulation comprises tapioca (a non-gelatin alternative).

In some embodiments, the composition or formulation further comprises citric acid.

In some embodiments, the composition or formulation further comprises acacia, gum acacia or derivatives thereof.

In some embodiments, the composition or formulation described herein further comprises a natural sweetener. In some embodiments, the natural sweetener is derived from the stevia plant. In some embodiments, the natural sweetener is stevia extract powder. In some embodiments, the natural sweetener is Luo Han Gou. In some embodiments, the natural sweetener comprises Monoammonium Glycyrrhizinate and/or Ammonium Glycyrrhizinate. In some embodiments, the natural sweetener is honey or an extract thereof. However, in some embodiments, the composition or formulation does not contain a natural sweetener such as stevia extract. In some embodiments, the composition or formulation does not contain stabilizers, artificial flavorings, colors, mycotoxins, simple sugars, as well asor toxic byproducts (e.g., Benzene, Hexane, heavy metals, etc.) from extraction methods.

In some embodiments, the composition or formulation further comprises one or more organic oils. In some embodiments, the one or more organic oils are selected from peppermint, sweet orange, ginger, lavender, tangerine, cherry and/or mango.

In some embodiments, methods for treating a disorder are described herein. In some embodiments, the methods comprise administering a therapeutically effective amount of a pharmaceutical composition or formulation described herein to a subject or patient in need thereof. In some embodiments, the melatonin is provided in an amount effective to aid the sleep of a subject. In some embodiments, the melatonin is provided in an amount effective to treat at least one symptom of seasonal affective disorder (SAD), insomnia, jet lag, or chronic cluster headaches.

In some embodiments, the disorder is selected from inflammation (chronic or acute), inflammatory bowel disease (IBS), Crohn's disease (CD), irritable bowel syndrome (IBS) with or without diarrhea or constipation, ulcerative colitis (UC), nausea, vomiting, anorexia, cachexia, all forms of pain (i.e. acute, chronic, neuropathic, and pain associated with or accompanying migraine headaches and cancer), gastrointestinal tract distress (i.e. heartburn, indigestion, stomachache, etc.), migraine headaches whether hormone mediated or not, chronic cluster headaches, seizures, postmenstrual syndrome (PMS), Cancer, neurodegenerative diseases including Lou Gehrig's disease, Huntington's disease, Alzheimer's dementia, Parkinson's disease and Parkinsonian-type symptoms; spinal-cord injuries, HIV/AIDS, agitation, sleep disorders such as insomnia, seasonal affective disorder (SAD), and jet lag; depression, muscle spasms, spasticity from multiple sclerosis, glaucoma, Autism Spectrum Disorder (ASD), Attention Deficit Hyperactivity Disorder (ADHD) with or without hyperactivity, Post-Traumatic Stress Disorder (PTSD), and anxiety disorders.

In some embodiments, use of a composition or formulation described herein for treating a disorder described herein is described. In some embodiments, the use of a composition or formulation described herein for treating a disorder selected from inflammation (chronic or acute), inflammatory bowel disease (IBS), Crohn's disease (CD), irritable bowel syndrome (IBS) with or without diarrhea or constipation, ulcerative colitis (UC), nausea, vomiting, anorexia, cachexia, all forms of pain (i.e. acute, chronic, neuropathic, and pain associated with or accompanying migraine headaches and cancer), gastrointestinal tract distress (i.e. heartburn, indigestion, stomachache, etc.), migraine headaches whether hormone mediated or not, chronic cluster headaches, seizures, postmenstrual syndrome (PMS), Cancer, neurodegenerative diseases including Lou Gehrig's disease, Huntington's disease, Alzheimer's dementia, Parkinson's disease and Parkinsonian-type symptoms; spinal-cord injuries, HIV/AIDS, agitation, sleep disorders such as insomnia, seasonal affective disorder (SAD), and jet lag; depression, muscle spasms, spasticity from multiple sclerosis, glaucoma, Autism Spectrum Disorder (ASD), Attention Deficit Hyperactivity Disorder (ADHD) with or without hyperactivity, Post-Traumatic Stress Disorder (PTSD), and anxiety disorders, is described.

In some embodiments, methods for making or manufacturing a composition or formulation described herein are described. In some embodiments, the method comprises (i) preparing or obtaining a cannabis extract, and (ii) adding melatonin to the extract in an amount sufficient to treat a sleep disorder of a subject that is administered or consumes the pharmaceutical composition or formulation. In some embodiments, the method further comprises mixing the composition or formulation with a base selected from polyethylene glycol, gelatin, pectin, tapioca, fatty acid and/or wax. In some embodiments, the base is PEG. In some embodiments, the base is gelatin. In some embodiments, the base is pectin. In some embodiments, the base is a gelatin alternative (e.g., tapioca). In some embodiments, the sleep disorder is insomnia, seasonal affective disorder (SAD), or jet lag.

In some embodiments, the compositions or formulations described herein avoid harmful preservatives (e.g., BHT, BHA) and stabilizers, artificial sweeteners and artificial colors, while addressing subtherapeutic dosing and optimizing the synergistic qualities of the ratios of the individual cannabinoids (either in their acid or neutral form), terpenes and flavonoids. Moreover, embodiments described herein allow for accurate and reproducible therapeutic effects along with ease of dosage adjustments.

It will be understood that certain ingredients can be added to the compositions described herein without materially affecting the basic and novel properties of the compositions described herein. For example, the compositions can include undisclosed and/or unclaimed ingredients that do not materially affect the basic and novel properties of the compositions described herein, therapeutic or otherwise. Examples of such ingredients include flavorings and sweeteners that provide a more pleasant taste and/or odor, but do not materially affecting the desired properties, therapeutic or otherwise, of the compositions described herein.

Other variations, embodiments and features of the present disclosure will become evident from the following detailed description, drawings and claims.

Defintions

The term "formulation" includes the compositions described herein and any additional components that are desired for administering the composition to a subject or for consumption of the composition by a subject. The term "formulation" includes suitable delivery systems or "dosage forms," such as but not limited to a tablet, capsule, lozenge, troche, tincture, suppository, transdermal patch, vaporizer or other inhalation device, or metered dose inhaler.

The term "polyethylene glycol" ("PEG") refers to any of a series of polymers $H(OCH_2CH_2)_nOH$ where n is greater than three and are used as a base for the pharmaceutical formulations and compositions described herein. As used herein, PEG followed by a number refers to the average molecular weight in daltons, for example PEG 1450 refers to PEG with an average molecular weight of 1450. As is understood by one of ordinary skill in the art, PEGs typically include molecules with a distribution of molecular weights (i.e., they are polydisperse). For example, the average molecular weight may include PEG molecules having a molecular weight of +/−20% or +/−10% (i.e., 10% greater than or less than) the average molecular weight. In one embodiment, PEG 1450 has a range of average molecular weight of 1305-1595. In one embodiment, the PEG has an average molecular weight of 1450+/−300.

The term "about" when used to modify a numerical value or range described herein includes normal variation expected by one of ordinary skill in the art of formulations. Thus, the term about can include from +/−1% to +/−10% variation in a numerical value or range, such as +/−1%, 2%, 3%, 4%, 5%, 6%, 7%, 8%, 9%, or +/−10% of the numerical value or range. It will be understood that any numerical value or range described herein can be modified by the term "about," even if the numerical value or range is not expressly modified by the term "about."

In some embodiments, the compositions and formulations described herein comprise, consist essentailly of, or consist of the recited ingredients.

BRIEF DESCRIPTION OF THE DRAWINGS

Not applicable.

DETAILED DESCRIPTION OF THE INVENTION

The compositions and/or formulations described herein are useful for the treatment and prevention of a wide range of disorders, including, for example, inflammation, inflammatory bowel disease (IBS), Crohn's disease (CD), irritable bowel syndrome (IBS), ulcerative colitis (UC), nausea, vomiting, anorexia, cachexia, all forms of pain (i.e. acute, chronic, neuropathic, and pain associated with or accompanying migraine headaches and cancer), gastrointestinal tract distress (i.e. heartburn, indigestion, stomachache, etc.), migraine headaches, seizures, postmenstrual syndrome (PMS), Cancer, neurodegenerative diseases like Lou Gehrig's disease, Huntington's disease, Alzheimer's dementia, Parkinson's disease and Parkinsonian-type symptoms, spinal-cord injuries; HIV/AIDS, agitation, insomnia, depression, muscle spasms, spasticity from multiple sclerosis, glaucoma, Autism Spectrum Disorder (ASD), Attention Deficit Hyperactivity Disorder (ADHD), Post-Traumatic Stress Disorder (PTSD), and anxiety disorders. The actives used in the compositions and/or formulations described herein affect the human physiology in positive ways including the improvement of the immune system, prevention or treatment of certain cancers, and reduction of inflammation. Those skilled in the art will recognize that the embodiments described herein may be used to treat any and all medical conditions that respond favorably thereto.

The effects of the following cannabinoids: CBD, CBDA, CBG, CBGA, CBC, CBCA, Delta-9 THCA, Delta-9 THC and/or Delta-8 THC (and others not well charaterized in the literature, recognizing that 144 cannabinoids have been identified at this point in time), as well as the very important group of physiologically active compounds called terpenes and flavonoids need to be present at certain percentages to optimize the clinical effects on each type of symptom and/or disease for which the product is being used. The embodiments of the present disclosure also recognize the importance of the ratios of each of the aforementioned actives. These cannabinoids are also temperature sensitive and the embodiments described herein recognize the significance of temperature during each relevant step of making the product. For instance, keeping the temperature controlled along with the amount of the acid form of THC and/or CBD may have a profound effect on certain conditions mentioned earlier.

Some of the drawbacks associated with prior art cannabinoid formulations surround the route of administration and the dosage form used. Ease of dosage adjustment is an important component with the use of cannabis as a treatment. The delivery system disclosed herein offers easy adjustment of the dose needed by the patient, which improves the overall outcome of the use of cannabis therapy.

In some embodiments, the dosage form is solid at room temperature. In one embodiment, the dosage form is a lozenge or troche. In either instance, the product may be refrigerated or frozen without harm. Advantageously, with a melting point of approximately >38° C. (100.4° F.), the lozenge or troche dissolves at body temperature within the mouth of a user where the majority of absorption takes place resulting in optimizing the dose absorbed and avoiding the variables of oral absorption and first pass metabolizm.

In some embodiments, the Formulation is manufactured by combining cannabis extracts with melatonin. In some embodiments, the melatonin is added such that the concentration is from 0.05% to 1.6% by weight of the composition and/or formulation. In some embodiments, polyethylene glycol with approximate average molecular weights of 1300 to 1650 g/mol, or any value between 1300 and 1650 g/mol, for example, 1300, 1350, 1400, 1450, 1500, 1550, 1600, 1650 g/mol, is combined with the cannabis extract and melatonin. In some embodiments, polyethylene glycol with approximate molecular weights of from 1300 to 8000 g/mol, or any value between 1300 and 8000 g/mol, for example 1300, 1350, 1400, 1450, 1500, 1550, 1600, 1650, 1700, 1750, 1800, 1850, 1900, 1950, 2000, 2500, 3000, 3500, 4000, 4500, 5000, 5500, 6000, 6500, 7000, 7500, or 8000 g/mol, is combined with the cannabis extract and melatonin. In some embodiments, additional ingredients such as specific forms of gum acacia, citric acid, stevia extract powder, oils of peppermint, and/or menthol are added at specific temperatures with a range of cannabis extracts providing specific doses that include the following compositions singularly or in combination: (i) Delta-9 Tetrahydrocannabinol in the decarboxylated form in doses ranging from 5 mg to 240 mg (0.5% to 25.26% by weight); (ii) Tetrahydrocannabinolic acid (THC-A in the natural acidic, non-decarboxylated form) in doses of 5 mg to 240 mg (0.5% to 25.26% by weight); (iii) Cannabidiol (CBD) in doses of 5 mg to 240 mg with a Delta-9 THC content less than or equal to 0.3 mg (making this dosage form legal in all states of the United States); and Cannabidiol (CBD) in doses of 5 mg to 240 mg (0.5 to 21.26% by weight) in combination with Delta-9 Tetrahydrocannabinol in a 53:1 ratio (CBD:THC), or down to a ratio of 0.001:1 (CBD:THC), of Delta-9 THC in the decarboxylated and non-decarboxylated forms at specific temperatures. Another possible active includes Delta-8 Tetrahydrocannabinol. Other oils such as sweet orange, ginger, lavender, mango, cherry, tangerine, etc., may be substituted or used in combination with oils of peppermint, menthol and cream de mint. The cannabinoid dosage range of the different doseage forms (i.e. troche, suppository, etc.) may increase to 500 mg with the use of pure Cannabidiol or Tetrahydrocannabinol (i.e., crystals) as well as other cannabinoids.

Temperature control is necessary in the processing of cannabis extracts. As a result, one of ordinary skill in the art would recognize and use temperatures necessary to optimize cannabinoid, terpene and flavonoid content and ratios. Temperatures in the range of approximately −109° F. to 212° F. (at normal atmospheric pressure; temperatures change with negative pressures which allow for extraction and processing using different methods), maintain certain percentages of all cannabinoids and retain natural terpene and flavonoid content in the extracts thereby resulting in more medicinal value being retained instead of isolating one active. Notwithstanding the importance of the natural mixture of actives, it is understood that one single active ingredient can be used in the dosage form providing its own unique physiologic and clinical value.

Depending on the embodiment, Cannabis, *C. sativa, C. indica, C. ruderalis* and hybrids in the raw material are used to create specific ratios of CBD to THC. Percentages range from 24000:1 CBD:THC (i.e., 240 mg CBD to 0.01 mg THC) to 1:24000 CBD:THC (i.e., 0.01 mg CBD to 240 mg THC). In another embodiment, percentages range 200,000:1 CBD:THC and 1:200,000 CBD:THC.

The embodiments of the present disclosure contemplate dosage forms with a total weight of between approximately 0.5 grams and 2.01 grams, depending on the formulation of the actives, and size of the tablet, capsule, lozenge or troche. The suppository dosage form may raise the total weight to up to 5.2 gm. These dosage forms can be used for all natural, acidic or neutral, semi-synthetic and synthetic derivatives of all cannabinoids. Handling and processing of the extract is significant in the proper delivery of the actives with the associated terpenes and flavonoids, all which synergistically work to improve the medicinal value of the cannabinoids chosen for the particular ailment under treatment.

In some embodiments, assembly of the dosage form (e.g., lozenge or troche) comprises: (i) preparing a proprietary base of polyethylene glycol with average molecular weights of about 1300 to 1650 g/mol, or any value between 1300 and 1650 g/mol, for example, 1300, 1350, 1400, 1450, 1500, 1550, 1600, 1650 g/mol, or an average molecular weight from about 1300 to 8000 g/mol, or any value between 1300 and 8000 g/mol, for example about 1300, 1350, 1400, 1450, 1500, 1550, 1600, 1650, 1700, 1750, 1800, 1850, 1900, 1950, 2000, 2500, 3000, 3500, 4000, 4500, 5000, 5500, 6000, 6500, 7000, 7500, or 8000 g/mol, by melting the PEG at a temperature of approximately 58° C. to 64° C. at normal atmospheric pressure; (ii) adding the desired cannabis extract in amount sufficient to treat the symptom or disease state (e.g., 20 mg CBD dose with 1-2 mg of THC is effective for treating patients with autism, arthritis, and seizures); (iii) adding melatonin to a concentration of 0.5 mg-16 mg per dosage form (or 0.05% to 1.6% by weight per dosage form); and (iv) adding solution to a dosge form mold device to deliver accuracy of dosage desired. Range of standard deviation is <5% in weight and less than 10% of stated active goals. In some embodiments, additional ingredients can be added that do not affect the therapeutic properties of the dosage form (e.g., the tablet, capsule, lozenge, troche suppository, transdermal patch or inhaled dose). Examples of additional ingredients include citric acid, gum acacia, natural sweeteners such as stevia extract or Magnasweet®; essential oils, flavoring and/or allergy avoidance.

An exemplary method of producing 900 troches comprises: (i) measuring 670 grams of PEG 1450 (or PEG having an average molecular weight of 1450+/−300; or PEG having an average molecular weight of 1500+/−300) (the 670 grams of PEG makes up approximately 75% to 90% total weight); (ii) melting the 670 grams of PEG to a maximum temperature of approximately 60° C.-70° C. (many devices work; stir/hot plate, heated mix/pump/delivery automation—if used under vacuum, temperatures will be lower under automation assembly lines); (iii) once the PEG is melted, adding powders (e.g., citric acid—0.17% to 1.2% by weight, acacia gum—0.08% to 2.0%, optionally stevia (and/or Luo Han Gou)—0.46% to 3.1% by weight, and/or Magnasweet®—0.02% to 0.06% by weight) and mixing until suspended uniformly; (iv) adding 1 mg to 500 mg of active CBD and THC to each troche in ratios of 24000:1 to 1:1500 (e.g., for a 5 mg troche add 2.5 mg of CBD and 2.5 mg of THC if a 1:1 ratio is desired and add 4.6875 mg of CBD and 0.325 mg of THC if a 15:1 ratio is desired. For a 240 mg troche add 120 mg of CBD and 120 mg of THC for a 1:1 ratio and 225 mg of CBD and 15 mg of THC if a 15:1 ratio is desired) (v) adding 0.5 to 16 mg of melatonin. In some embodiments, 2 ml to 26.22 ml of essential oils (e.g., 20.2 ml of peppermint, 4.6 ml of menthol (made by dissolving 10 gm menthol crystals into 6 ml of peppermint oil and 2 ml of 99.9% ETOH) and 1.5 ml of cream de mint are added, and mixed to uniformity (the concentration of active oil extract is variable to determine total volume of oil and base to be added). The temperature is maintained between approximately 58° C. and 63° C. After the ingredients are completely mixed, a micro pipette is used to deliver 900 micro liters per troche (for the dosage form of 0.9725 gm/troche); and the mixture is allowed to cool at room temperature.

Another exemplary method of producing 900 troches each including 60 mg of THC with approximately 4 mg of CBD and 6 mg of melatonin comprises: (i) measuring 767 gm of PEG 1450 (or PEG having an average molecular weight of 1450+/−300; or PEG having an average molecular weight of 1500+/−300) (in this formulation the PEG makes up approximately 87% of total weight, based on a 62.5% THC oil containing 5.1% CBD); (ii) melting the 767 gm of PEG to a maximum temperature of approximately 60° C.-70° C. (many devices work; stir/hot plate, heated mix/pump/delivery automation—if used under vacuum, temperatures will be lower under automation assembly lines); (iii) once the PEG is melted, adding 86.4 gm stated concentration cannabis extract oil; (iv) adding 5.4 gm of melatonin; (v) adding a mixed set of powders (e.g., citric acid—0.17% to 1.2% by weight, acacia gum—0.08% to 2.0% by weight, optionally stevia (or Luo Han Gou)—0.46% to 3.1% by weight, and/or Magnasweet®—0.02% to 0.06% by weight) and mixing until suspended uniformly; (vi) adding 10 ml of essential organic oils (e.g., 9.7 ml sweet orange oil and 0.3 ml organic peppermint oil); (vii) mixing to uniformity, maintaining temperature between approximately 58° to 63° C.; (viii) once completely mixed using a micro pipette to deliver 900 micro liters per troche (for the dosage form of 0.9725 gm/troche); and (ix) allowing mixture to cool at room temperature.

It will be recognized by those skilled in the art that the formulations set forth above, are exemplary such that variations fall within the spirit and scope of the present disclosure. For example, the amount of cannabis extract oil used may vary based on concentration. More specifically, when using 560 mg THC/1 gm oil versus 764 mg THC/1 gm oil, the PEG base volume changes appropriately to maintain volume and correct dose, but density and weight changes. Moreover, different oils may be used in different amounts. For example, ginger is a potent oil such that a few drops may suffice whereas other oils may be used in units of milliliters. The combinations of oils may also differ. For example, a formulation may include peppermint oil but no extra menthol or cream de mint while another formulation may use ginger, orange and mint oil. That is, the oils provide a desired level of flavoring in addition to the therapeutic value of oils (e.g., peppermint oil).

In some embodiments, the formulation or dosage form can be made using three ingredients comprising or selected from 1) a base selected from PEG, gelatin, pectin, tapioca, agar, fatty acid and/or wax, 2) cannabis extract, and 3) melatonin. Or in another embodiment, the formulation or dosage form can be made using four ingredients comprising or selected from 1) a base selected from PEG, gelatin, pectin, tapioca, agar, fatty acid and/or wax, 2) cannabis extract, 3) melatonin and 4) an essential organic oil. Or in another embodiment, the dosage form can be made using ingredients comprising or selected from a base selected from PEG, gelatin, pectin, tapioca, agar, fatty acid and/or wax, cannabis extract, melatonin, and one or more of the following: gum acacia, citric acid, stevia extract powder, Luo Han Gou or, Monoammonium Glycyrrhizinate and Ammonium Glycyrrhizinate, and honey or honey extract.

The embodiments described herein demonstrate an improved efficacy that is unexpected compared to utilizing the same dose of the same active source of cannabis oil. In one particular example, the formulation comprising PEG, melatonin and high dose mint oil formula provides unexpected results as described herein.

In one embodiment, a high concentration (99%-99.9%) CBD derived from hemp is used to achieve the desired ratio. In other embodiments, the ratios are determined by the strain of cannabis that includes different amounts of CBD and THC.

In embodiments wherein the composition comprises a pharmaceutical product, the dosage forms described herein provide clear separation from the confusion associated with traditional preparations of natural cannabinoid infused products, including candy bars, chocolate, butter, baked goods, etc., that produce unreliable and varied clinical responses that are not always the same or reproducible. The use of the dosage forms described herein offers a method of reduced variability in the pharmacokinetics of the cannabinoids resulting in clinical outcomes that are consistent from dose to dose.

Any alterations and further modifications of the compositions and/or formulations described herein, which would normally occur to one skilled in the relevant art and having possession of this disclosure, are to be considered within the scope of the instant claims. All publications, patents, and patent publications described herein are incorporated by reference in their entirety for all purposes.

What is claimed is:

1. A formulation comprising a cannabis extract and melatonin, wherein the cannabis extract comprises Cannabidiol (CBD) at a concentration of 99%-99.9%, and 0.5 mg to 16 mg melatonin per individual formulation.

2. The formulation of claim 1, wherein the melatonin is present at a concentration of 0.05% to 1.6% by weight.

3. The formulation of claim 1, further comprising a base selected from polyethylene glycol, gelatin, agar, tapioca, and pectin.

4. The formulation of claim 3, wherein said polyethylene glycol has an average molecular weight of 1450+/−300.

5. The formulation of claim 1, further comprising one or more of the following: gum acacia, citric acid, stevia extract powder, Luo Han Guo, Monoammonium Glycyrrhizinate and Ammonium Glycyrrhizinate.

6. The formulation of claim 1 further comprising one or more organic oils.

7. The formulation of claim 6, wherein said one or more oils are selected from peppermint, sweet orange, ginger, tangerine, lavender and/or mango.

8. The formulation of claim 1, further comprising menthol and/or cream creme de mint.

9. The formulation of claim 1 wherein said cannabis extracts comprise one or more of the following: (i) Delta-9 Tetrahydrocannabinol in the decarboxylated form; (ii) Tetrahydrocannabinolic acid in the natural, non-decarboxylated form; (iii) Cannabidiol with a Delta-9 THC content less than or equal to 0.3 mg/g; and (iv) Delta-8 Tetrahydrocannabinol.

10. The formulation of claim 1, wherein the cannabis extract comprises one or more of cannabinoids, terpenes and flavonoids.

11. The formulation of claim 1, wherein the formulation is provided in a tablet, capsule, lozenge, troche, suppository, tincture, transdermal patch, per inhalation from a vaporizer or metered dose inhaler.

12. A method for making or manufacturing the formulation of claim 1, the method comprising:
(i) preparing a cannabis extract, and
(ii) adding melatonin to the extract in an amount sufficient to treat a sleep disorder in a subject.

13. The formulation of claim 1, wherein the cannabis extract comprises 5 mg to 240 mg CBD and less than or equal to 0.3 mg Delta-9 THC.

14. The formulation of claim 1, wherein the formulation is a tablet, capsule, lozenge or troche and the total weight is between 0.5 grams and 2.01 grams.

15. The formulation of claim 1, wherein the formulation is a suppository and the total weight is between 0.5 and to 5.2 grams.

16. The formulation of claim 3, wherein said polyethylene glycol comprises 75% to 90% by weight.

17. A method of treating a subject having a sleeping disorder, the method comprising administering a therapeutically effective amount of the formulation of claim 1 to the subject.

18. The method of claim 12, wherein the sleep disorder is insomnia, seasonal affective disorder (SAD), or jet lag.

19. The method of claim 12, further comprising mixing the formulation with a base selected from polyethylene glycol, gelatin, pectin, agar, tapioca, fatty acid and wax.

20. The method of claim 19, further comprising adding one or more of the following: gum acacia, citric acid, stevia extract powder, Luo Han Guo, Monoammonium Glycyrrhizinate and Ammonium Glycyrrhizinate, honey or extract thereof.

* * * * *